US007416526B2

(12) United States Patent
Chen

(10) Patent No.: US 7,416,526 B2
(45) Date of Patent: Aug. 26, 2008

(54) ARTIFICIAL INSEMINATION DEVICE IN ANIMALS

(76) Inventor: Sheng-Jui Chen, No. 14, Lane 291, Shin-Te St., Pyng-Jenn City, Taoyuan (TW)

( * ) Notice: Subject to any disclaimer, the term of this patent is extended or adjusted under 35 U.S.C. 154(b) by 120 days.

(21) Appl. No.: 11/172,844

(22) Filed: Jul. 5, 2005

(65) Prior Publication Data

US 2007/0010705 A1 Jan. 11, 2007

(51) Int. Cl.
*A61B 17/43* (2006.01)

(52) U.S. Cl. .................................................... 600/35

(58) Field of Classification Search ............ 600/33–35; 604/515, 906, 93.01, 96.01
See application file for complete search history.

(56) References Cited

U.S. PATENT DOCUMENTS

| | | | | |
|---|---|---|---|---|
| 5,899,848 | A * | 5/1999 | Haubrich | 600/35 |
| 6,004,260 | A * | 12/1999 | Thompson | 600/33 |
| 6,860,235 | B2 * | 3/2005 | Anderson et al. | 119/174 |

* cited by examiner

*Primary Examiner*—Charles A. Marmor, II
*Assistant Examiner*—Christine D Hopkins
(74) *Attorney, Agent, or Firm*—Rosenberg, Klein & Lee

(57) ABSTRACT

An artificial micro-insemination device for animals is disclosed. The device has an elastic insemination sheath amassed in compressed state between the nozzle passage and the forward portion of center orifice of catheter tube, where the rear end of the elastic insemination sheath is secured to the front part of nozzle, characterized in which the catheter tube and nozzle are inserted into the uterus of animal with the nozzle positioned posterior to the first cervical ring, and by the pressure of semen dispenser squeezing in semen from the rear end of catheter tube, the extension member of the soft elastic insemination sheath instantaneously extend outward from the front part of nozzle and extends freely along the cervical tract to reach uterus, where coupled with uterine contraction, semen fluid squeezed into the extension member of insemination sheath is expelled into the uterus or the two ducts to uterine horns via the prearranged slits on the front part of extension member. Such design not only reduces the backflow of semen, it also offers the economic benefit of using minimal semen and improves the efficiency of artificial insemination.

8 Claims, 19 Drawing Sheets

ARTIFICIAL INSEMINATION DEVICE IN ANIMALS

BACKGROUND OF THE INVENTION

1) Field of the Invention

The present invention relates to an artificial insemination device for animals, more particularly, a simple device that is easy and convenient to use and allows animal semen to reach the two ducts to uterine horns or the uterus swiftly and smoothly, thereby improving the success rate of artificial insemination and effectively saving the amount of semen needed. The invention herein requires minimal amounts of insemination semen and offers economic benefit. It also renders artificial insemination safer, more hygienic, and more humane.

2) Description of the Prior Art

The assembly and operation of conventional artificial insemination device for animals as shown in FIG. 1 and FIG. 2, typically comprises a plastic catheter tube 10 of certain hardness and a nozzle 20 made of softer material installed protrusively on the front end of catheter tube 10. When artificial insemination is carried out, the catheter tube 10 and nozzle 20 are inserted along the vagina 11 of female animal body 1 until the nozzle 20 at the front penetrates into cervical tract 12. Subsequently, the insertion tube 31 of the semen dispenser (bag or syringe) 30 containing the animal semen is inserted into the rear end of catheter tube 10, and as the operator continuously squeezes the semen dispenser (bag or syringe) 30, the semen contained therein is ejected into the cervical tract 12 through the nozzle 20 of catheter tube 10, where the uterus 13 contracts to draw in semen from cervical tract 12. Although the configuration and operation of such artificial insemination device achieve the purpose of artificial insemination in animals effectively, there are some drawbacks:

1. After the catheter tube 10 penetrates the vagina 11 of female animal body 1, the nozzle 20 at the front is pushed approximately to the position of first cervical ring 121 of cervical tract 12, but there remains considerable distance between the first cervical ring 121 and the uterus. Although the contraction of uterus 13 could draw in the semen from cervical tract 12, a large amount of semen ejected from the nozzle 20 initially accumulates at the position of first cervical ring 121 and cannot instantly flow into the uterus 13. What happens most frequently is that the semen accumulated at the first cervical ring 121 often backflows outside the vaginal orifice 111. As such, not only semen is wasted, the amount of semen that flows into the uterus 13 is proportionately lessened, hence decreasing the probability of successful insemination.

2. In response to the problem of semen backflow, operators commonly dilute the semen fluid many folds (typically 5 cc is diluted into 50-120 cc) and enlarge the inner diameter of catheter tube to accommodate and provide more semen fluid for insemination. But the massive dilution of semen fluid apparently reduces the rate of fertilization and the number of fetus, while using more semen leads to waste directly.

3. As described above, the semen in catheter tube 10 is directly released from the nozzle 20, and when nozzle 20 penetrates the cervical tract 12 from outside the female animal body 1, the accidental admittance of contaminants from outside the body or the vagina 11 is difficult to avoid as the semen flows into the uterus 13. As such, the risk of bacteria infection and inflammation of the vagina, cervical tract, and even the uterus of the animal during artificial insemination is high and, at the same time, the safety of fetus carried in the uterus 13 is jeopardized.

4. To improve the success rate and safety of artificial insemination, the operation of artificial insemination requires professional personnel (such as veterinarians or specialized technical personnel) and, as such, to big animal farms (such as pig farmers), it incurs heavy economic burden and demands considerable professional manpower.

5. After the operator utilizes the catheter tube 10 and nozzle 20 to penetrate the vagina 11 and cervical tract 12 of female animal body 1, he has to use one hand to hold the rear end of catheter tube 10 and the other hand to grip and squeeze the semen dispenser 30, which is apparently more troublesome, inconvenient, cumbersome, and time consuming in operation.

To render animal artificial insemination process more efficient and humane, some operators would use accessory devices. As shown in FIG. 3, such devices include an AI Buddy 40, an elastic saddle-like apparatus resembling the two front legs of an animal, wherein a connector 50 with open posterior is installed at the rear end of catheter tube 10, with a positioning strap 41 disposed between the AI Buddy 40 and the connector 50; as such, during the artificial insemination procedure, the operator straddles the AI Buddy 40 over the back of the female animal 1 such that the female animal feels that a male animal has mounted with its two front legs, a guide bush 60 is then placed at the vaginal orifice 111 of female animal body 1 and after the catheter tube 10 and nozzle 20 penetrate the vagina 11 and reaches the cervical tract 12 through the guide bush 60, the rear end of catheter tube 10 is flexed upward and directly secured by the positioning strap 41 connected to the AI Buddy 40; following the ingress of a semen dispenser 30 insertion tube 31 into the connector 50, the operator only has to squeeze the semen dispenser 30. In such approaches, the operator needs to use both hands at the same time, one for grasping the catheter tube 10 and one for squeezing the semen dispenser 30, a procedure that is troublesome and time consuming, but nevertheless an effective improvement. However, existent shortcomings that have not been improved include semen backflow that wastes semen, which is uneconomical and lowers insemination success rate; the easy inflow of contaminants from the outside of the female animal body into the vagina, cervical tract, and uterus that endanger the health of the female animal and fetus carried in the uterus; and the requiring of specialized personnel for operation, which is uneconomical and involves additional manpower.

To increase the success rate of artificial insemination, an improved artificial insemination device for animals as shown in FIG. 4 and FIG. 5 (U.S. Pat. No. 5,899,848) has been disclosed, which features a balloon 16 attached to nozzle 20 of catheter tube 10. The balloon 16 is folded or tucked completely within the forward end of passage of nozzle 20 with a plurality of perforations 29 formed within the periphery of balloon. When semen dispenser is inserted into nozzle 20 of catheter tube 10, the balloon 16 is inflated by the semen forced therein, and the semen is subsequently expelled through the perforations 29 due to the uterine contractions acting upon the balloon 16 at cervical tract. Undeniably, the device just mentioned is an improvement over conventional artificial insemination devices that have the drawbacks of massive backflow of semen and easily bringing contaminants from outside of female animal body into the vagina, cervical tract and even uterus, hence endangering the health of animal and fetus. But given that after nozzle 20 of catheter tube 10 is extended inward to the position of first cervical ring of cervical tract, the balloon 16 in inflated shape that is exposed under the force of semen merely reaches the forward portion of passage of nozzle 20, still around the first cervical ring. Under the circumstance that there remains considerable distance between the inflated balloon 16 that carries semen fluid and the uterus, the semen expelled under the action of uterine contraction is unable to reach uterus swiftly and efficiently and some would backflow, resulting in waste. To make sure more semen enters uterus, the inner diameter of catheter tube 10 has to be made larger to accommodate more semen, which does not improve the uneconomical use of semen seen in conventional artificial insemination devices.

Referring to FIG. 6 and FIG. 7, another artificial insemination apparatus for animals is disclosed (U.S. Pat. No. 6,526,917), wherein the front end opening 421 of catheter tube 420 is inserted into a sheath-like membrane 410 and the leading edge 412 of membrane 410 is snapped into a positioning ring 422 of catheter tube 420. Subsequently, nozzle 440 is inserted into the front end of catheter tube 420 to immobilize membrane 410. After nozzle 440 is inserted into the front end of catheter tube 420, the various components including the member 410 sandwiched between nozzle 440 and the catheter tube 420 can be further secured to each other by being sonically welded or heat staked. The object of such artificial insemination assembly is to cause the tip 411 of sheath-like membrane 410 to begin unfolding in an inside-out manner not unlike removing one's sock by pulling from the open end when semen is squeezed into the rear end of catheter tube 420 and enters the uterus along the cervical tract where semen is ejected from the opening of tip 411 to enhance the efficiency of insemination, prevent the entry of contaminants into the uterus, and prevent the backflow of semen. Such artificial insemination apparatus is more effective in comparison with prior art. But it still has some drawbacks in actual implementation:

1. Given that membrane 410 is inserted from the opening of catheter tube 420 and secured to nozzle 440 via a leading edge 412, the tip 411 of membrane, when squeezed inside-out under the pressure of semen, must pass through the pathway B (FIG. 6) of nozzle 440 before entering the cervical tract of animal. Thus in order for membrane 410 to enter the uterus of animal, it must have certain length. As we know, the longer the membrane, greater squeeze force to expose it outside the nozzle is required, rendering the whole operation more troublesome. In particular when the semen dispenser is in bag shape, the force generated from squeeze is not as much as that of bottle or syringe, which construes a limitation in implementation.

2. Given that the leading edge 412 of membrane 410 is snapped into the positioning ring 422 of catheter tube 420, membrane 410 is tightly attached to the periphery of tube 420 under certain tension, and subsequently nozzle 440 is tightly conjoined to the periphery of membrane 410. What happens most frequently is that when the membrane 410 under tension is pushed by the exertion of nozzle 440, perforation tends to occur around the edge of front end of catheter tube 420 (shown as C in FIG. 6). In such event, when semen is squeezed into catheter tube 420, the perforation would cause air leakage, which keeps membrane 410 from being squeezed out quickly and smoothly, thereby resulting in poor execution or even the failure of artificial insemination.

3. As perforation C on membrane 410 is totally covered by nozzle 440, the quality of the apparatus becomes uncertain since quality control inspection is difficult to carry out. Similarly the performance of the apparatus also becomes questionable.

4. Given that membrane 410 is inserted into catheter tube 420 from its opening 421, the inner diameter of catheter tube 420 (i.e. the hollow space 424) must be bigger. But bigger tube directly increases the consumption of semen, the same as in prior art. Such apparatus apparently does not offer the economic benefit of saving the usage of semen.

5. To prevent trauma to the animal during artificial insemination, the nozzle is usually made of elastomeric material. If the force used is improper or the animal does not stay still during artificial insemination, the front part of nozzle is prone to deformation or bend which might block the semen pathway. Under the circumstances, it is likely that the membrane 410 disposed inside catheter tube 420 will not extend under pressure to achieve artificial insemination.

SUMMARY OF THE INVENTION

The primary object of the present invention is to provide an artificial insemination device for animals, characterized in which an elastic insemination sheath is disposed between the nozzle passage and the forward portion of center orifice of catheter tube an the rear section of said elastic insemination sheath is secured to the front part of nozzle. When semen is squeezed into the catheter tube which causes the insemination sheath to unfold gradually under pressure, the length of insemination sheath that enters into the uterus along cervical tract is actually shorter as measured from the front part of nozzle. As such, the pressure needed to push the insemination sheath outward is effectively reduced, which renders the practice of artificial insemination more convenient. The movement of insemination sheath extending into the uterus is also made smoother, thereby enhancing the efficiency of artificial insemination.

Another object of the present invention is to provide an artificial insemination device for animals, wherein by making the rear end of insemination tube directly snapped over the front part of nozzle and disposing a neck ring made of slightly rigid material to brace the opening of nozzle passage, the assembly of insemination sheath is less prone to perforation and inspection of the integrity of the assembly is facilitated. Moreover, the front part of nozzle is less likely to deform or bend, hence keeping the nozzle passage unblocked all the time.

A further object of the present invention is to provide an improved artificial insemination device for animals, wherein the insemination sheath is tucked inwardly into nozzle through its front part and disposed in compressed state between the forward portion of center orifice of catheter tube and nozzle passage, instead of being inserted completely into the catheter tube. As such, the inner diameter of the catheter tube can be made smaller. Also, as the insemination sheath can effectively carry semen into uterus without the concern of backflow when under pressure, the semen used does not require massive dilution, while only more concentrated semen in small amount needs to be injected into the catheter tube. Thus the present invention not only offers the economic benefit of saving the semen used, the fertilization rate and the number of fetus are also expected to increase.

Yet another object of the present invention is to provide an artificial insemination device for animals, wherein after the insemination sheath is inserted into the nozzle passage, the portion of sheath situated at the passage opening has a guide member that unfolds in an inside-out manner. When semen is squeezed into the catheter tube, the guide member concurrently guides the whole assembly of insemination sheath to unfold inside-out and extend forward, rendering the operation of artificial insemination more efficient.

The objects, features and effects of the invention are described in details below with accompanying drawing and embodiments.

DETAILED DESCRIPTION OF THE PREFERRED EMBODIMENTS

Figure 8:
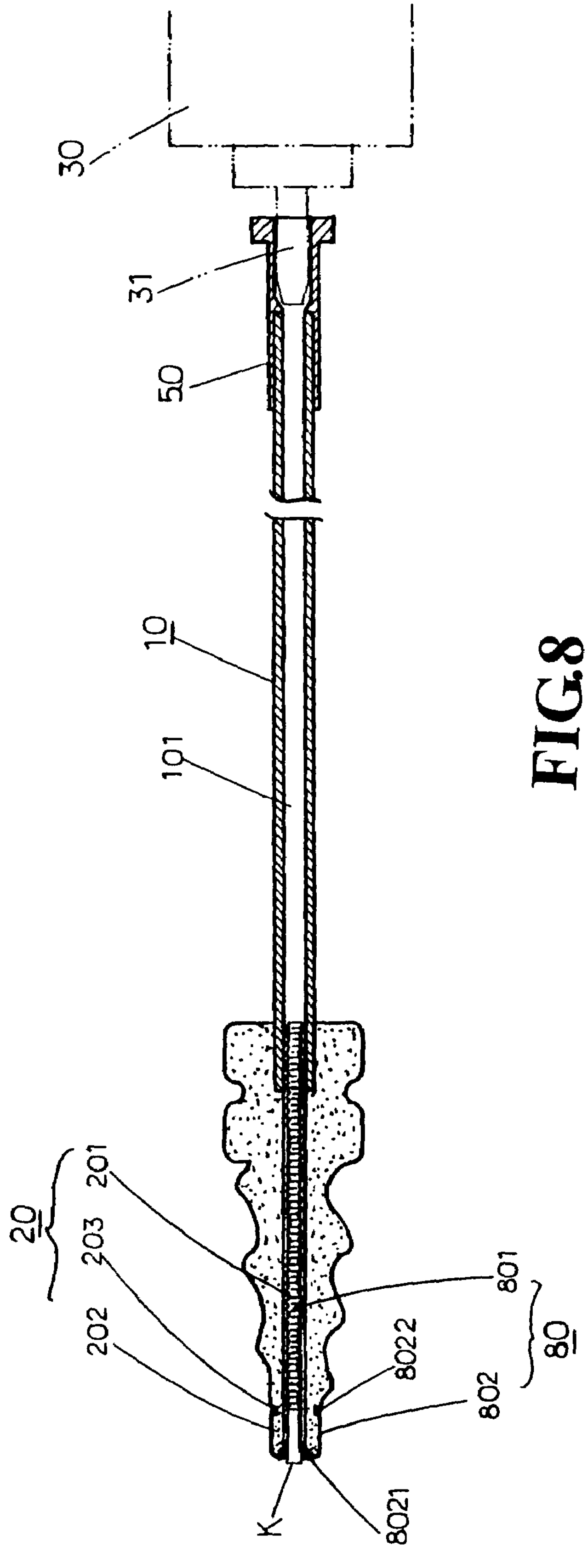
FIG. 8 is a schematic view of the present invention.
Figure 9:
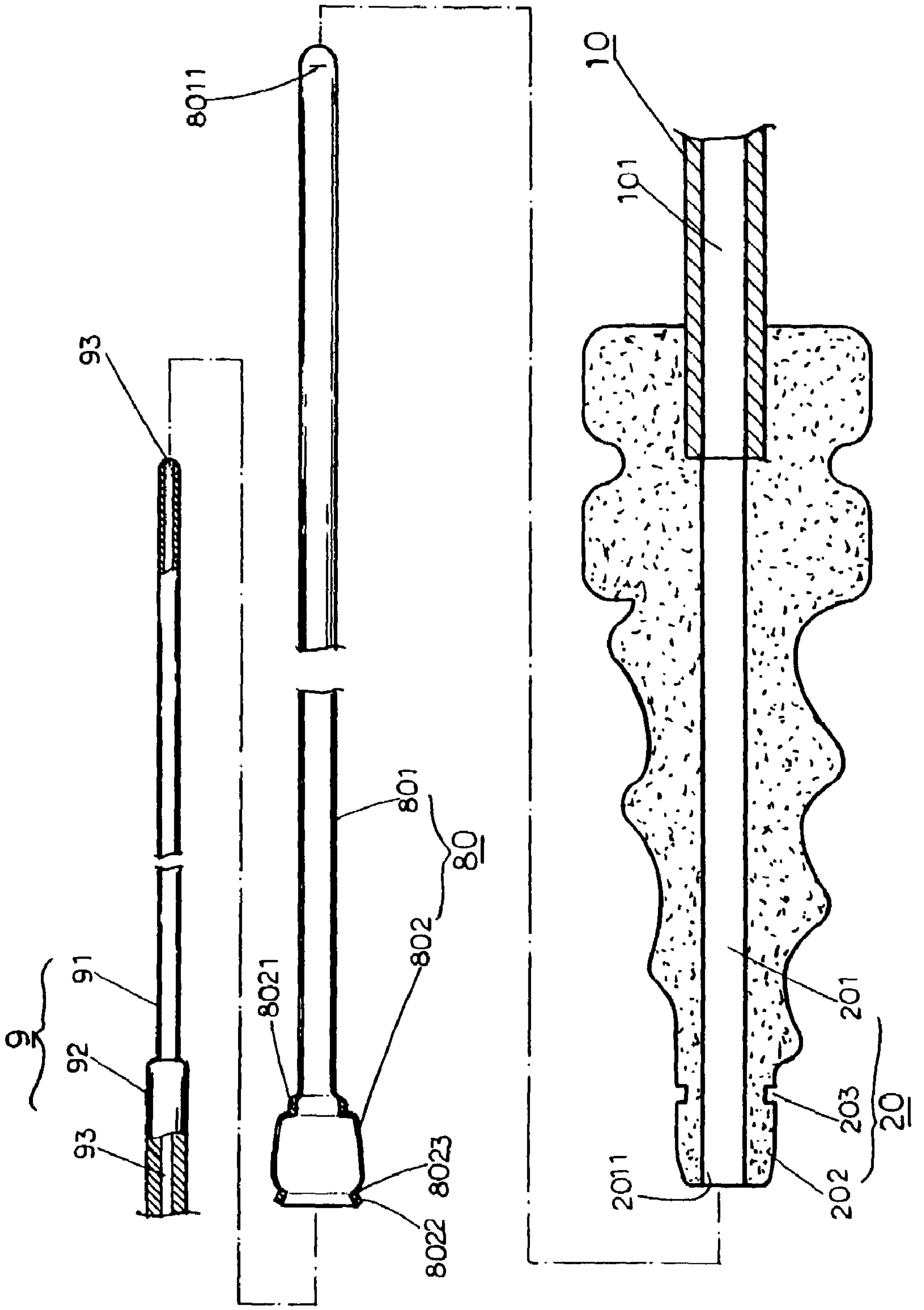
FIG. 9 is a schematic view of the catheter tube, elastic insemination sheath, and air rod in separated state.
Figure 10:
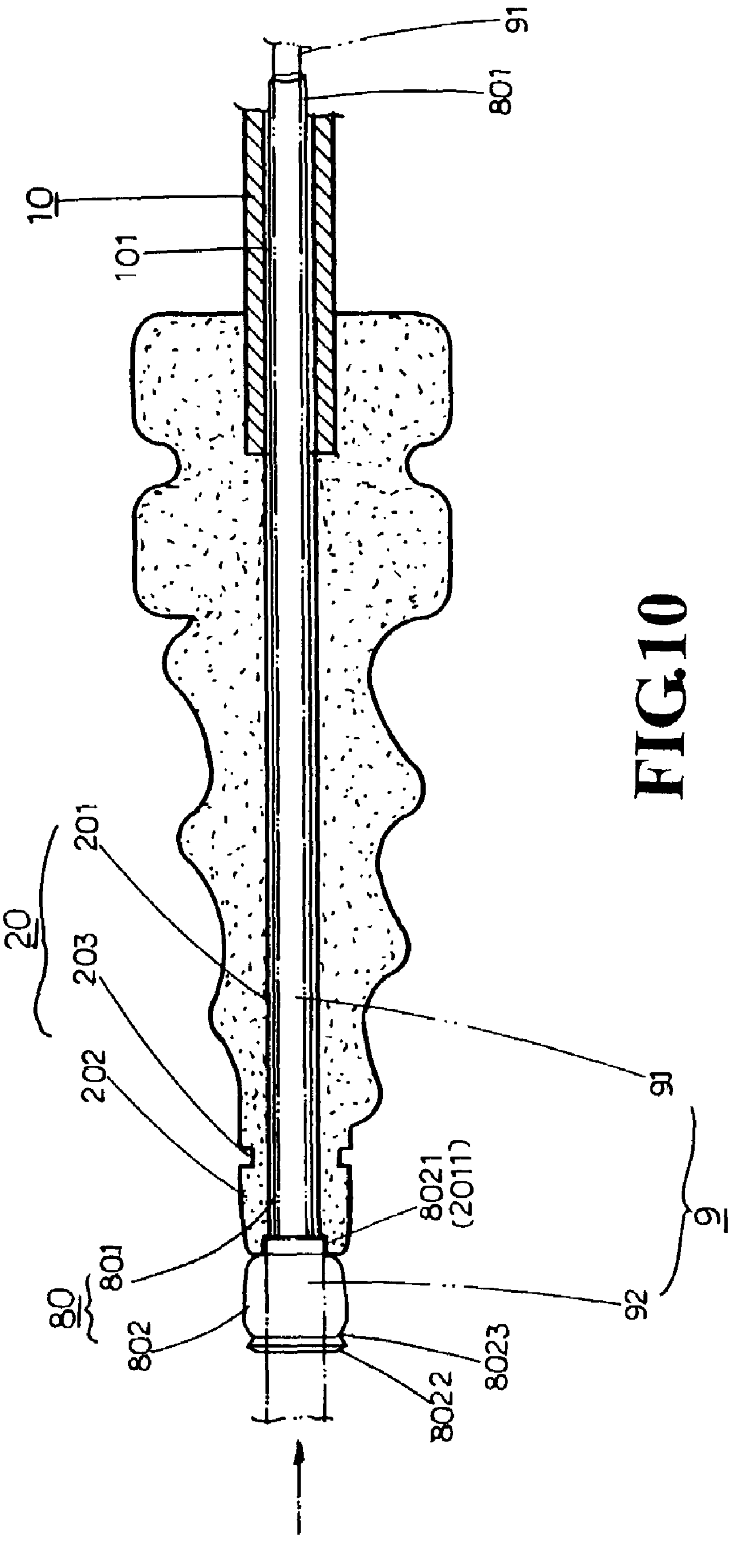
FIG. 10 is a schematic view of elastic insemination sheath tucked into the catheter tube according to the invention.

As show in FIG. 8, the artificial insemination device for animals according to the invention features an elastic insemination sheath 80 amassed in compressed state between the forward portion of center orifice 101 of catheter tube 10 and the passage 201 of nozzle 20, and the rear end of said elastic insemination sheath 80 is secured to the front part of nozzle 20. That is, as shown in FIGS. 9, 10, 11, 12, and 13, the elastic insemination sheath 80 is a membrane-like sheath made of balloon or condom material such that it possesses softness and elastic stretch characteristics and comprising an extension member 801 and a strap member 802. The extension member 801 has an elongated shape with slits juxtaposing along the two sides of its front end; the strap member 802 is bigger than extension member 801 with a small, thicker and more rigid neck ring 8021 in the front connected to the extension member 801 and a thicker strap ring 8022 at the back. A strap edge 8023 that tapers towards the center is disposed anterior to strap ring 8022.

The extension member 801 of insemination sheath 80 has an outer diameter smaller than that of the center passage 201 of nozzle 20 and the center orifice 101 of catheter tube 10 that allows it to be placed into nozzle passage 201 and center orifice 101 of catheter tube without difficulty.

The strap member 802 of insemination sheath 80 is configured slightly smaller than the positioning member 202 at the front part of nozzle 20, while the neck ring 8021 at the front of strap member 802 is configured slightly bigger than the passage 201 of nozzle 20, and the strap ring 8022 at the back of strap member 802 seats exactly into a prearranged seat groove 203 on the positioning member 202 of nozzle 20.

Figure 11:
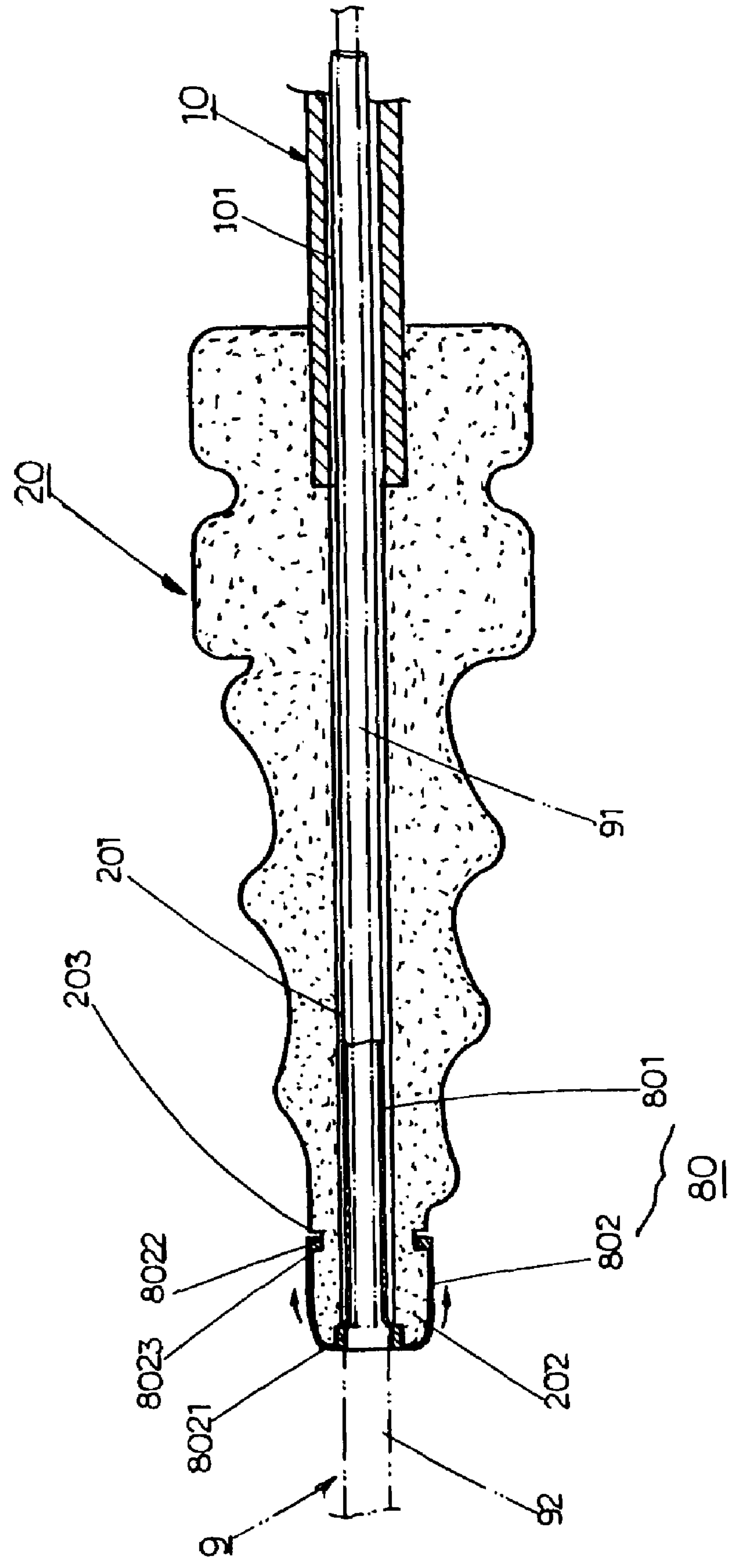
FIG. 11 is a schematic view of the strap member of elastic insemination sheath according to the invention secured to the nozzle.

That is, the elastic insemination sheath 80 has the front end of extension member 801 tucked into nozzle 20 from its front passage opening 2011 and the more rigid neck ring 8021 at the front of strap member 802 seated at the front passage opening 2011 of nozzle for support. Given that strap member 802 is slightly smaller than the positioning member 202 of nozzle 20 and it is elastic and stretchable, the operator can push the strap member 802 in reverse direction along the periphery of nozzle positioning member 202 to enfold it completely. Also because the strap ring 8022 at the back of strap member 802 is thicker and has stronger tightening force, and a strap edge 8023 which tapers towards the center is disposed anterior to strap ring 8022, giving strap ring 8022 tighter clamping power; when strap member 802 gradually enfolds the nozzle positioning member 202 and aligns strap ring 8022 with the seat groove 203 on nozzle positioning member 202, the strap ring 8022 consequently and quickly seats into the seat groove 203 in a press-down manner. The strap edge 8023 also acts to tighten up to make sure the union of insemination sheath 80 and nozzle 20 is secure and stable that does not separate easily (FIG. 11).

After the extension member 801 of insemination sheath 80 is tucked into the nozzle 20 from the front passage opening 2011 with strap member 802 tightly enfolding nozzle positioning member 202, the extension member 801, with the aid of a fixator or a mechanical device, will compress gradually towards the back until it reaches the position between the passage 201 of nozzle 20 and the forward portion of center orifice 101 of catheter tube 10.

There are a variety of means to amass the extension member 801 of insemination sheath 80 in compressed state at the location between nozzle passage 201 and the forward portion of center orifice 101 of catheter tube 10. In an embodiment of the invention, an air rod 9 is employed. Air rod 9 has a round and smooth body and is comprised of a sheathing member 91, a positioning member 92, and a through air hole disposed at the center; wherein the sheathing member 91 approximates the extension member 801 of insemination sheath 80 in length and can be disposed directly throughout the inside of extension member 801; positioning member 92 is slightly smaller than the neck ring 8021 on the strap member 802 of insemination sheath 80 for neck ring 8021 to clasp fittingly over its periphery.

In the assembly of insemination sheath 80 with air rod 9, insemination sheath 80 is first folded over air rod 9 with extension member 801 and neck ring 8021 of strap member clasping respectively the sheathing member 91 and positioning member 92 of air rod 9; next, insert the air rod 9 from the front passage opening 2011 of nozzle 20 to bring the extension member 801 of insemination sheath 80 into the passage 201 of nozzle 20 and the center orifice 101 of catheter tube 10 and position the neck ring 8021 of strap member 802 at the front passage opening 2011 of nozzle 20; the operator pushes the strap member 802 inwardly in reverse direction along the periphery of nozzle positioning member 202 until the strap ring 8022 and strap edge 8023 seat directly into the prearranged seat groove 203 on nozzle 20 to complete the assembly of insemination sheath 80 in nozzle 80; the operator then extracts air through the center air hole 93 of air rod 9 to let the front end of extension member 801 of insemination sheath 80 suck to the front end of sheathing member 91 of air rod 9; as the operator withdraws the air rod 9 slowly, the extension member 801 of insemination sheath 80 will squeeze backward along with the outward movement and naturally assemble in compressed state between the nozzle passage 201 and the forward portion of center orifice 101 of catheter tube 10.

In light that the strap member 802 of insemination sheath 80 is securely strapped to the front part of nozzle 20 and the extension member 801 is pliable, when the air rod 9 is withdrawn gradually, it is easy for extension member 801 to form a compressed shape, and moreover, the separation of the entire insemination sheath 80 from nozzle 20 is not a concern. After the extension member 801 is amassed in compressed state at the desired position, the air rod 9 will stop air extraction so that the front end of extension member 801 of insemination sheath 80 is no longer sucked to the front end of sheathing member 91 of air rod 9. As such, air rod can be withdrawn smoothly and the assembly of insemination sheath 80 is completed swiftly.

Figure 12:
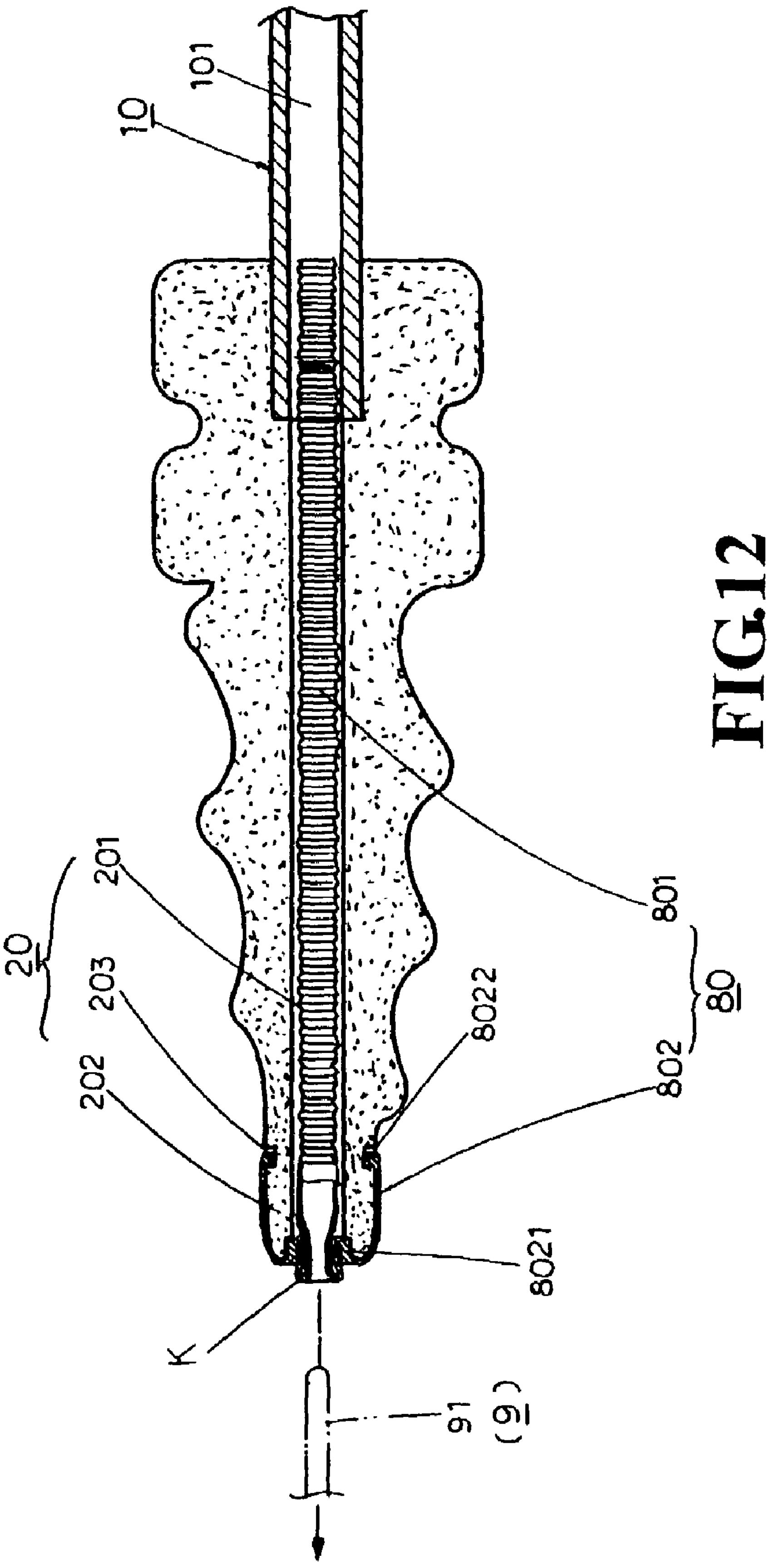
FIG. 12 is a schematic view of the extension member of elastic insemination heath according to the invention in compressed state.
Figure 13B:
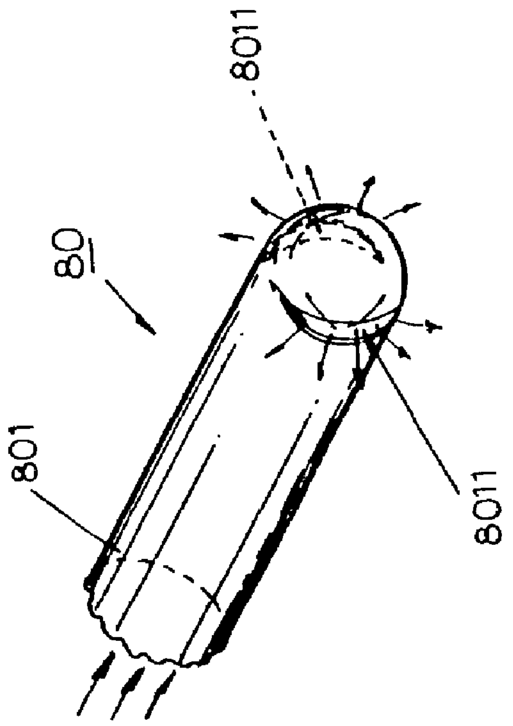
FIGS. 13A and 13B show the slits at the front of extension member of elastic insemination sheath according to the invention in closed and open state.
Figure 13A:
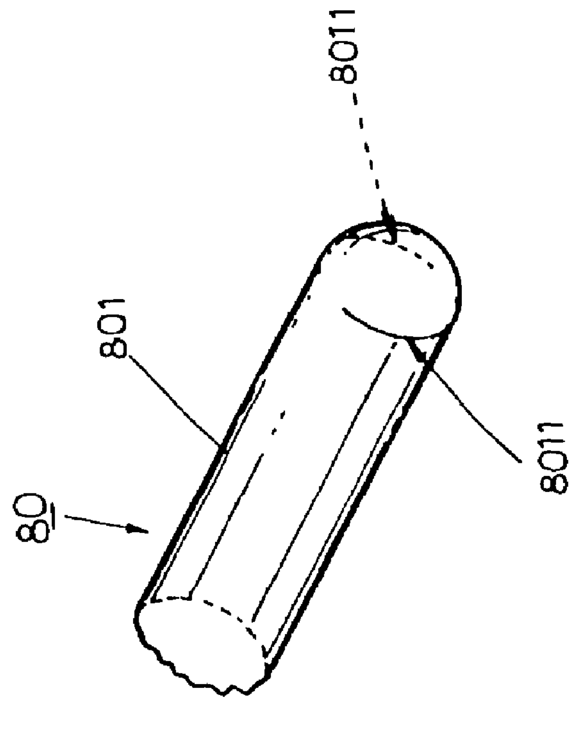

Referring to FIG. 12 and FIG. 13, after the extension member 801 of insemination sheath 80 is amassed in compressed state between nozzle passage 201 and the forward portion of center orifice 101 of catheter tube, the section of extension member 801 situated at the front passage opening 2011 of nozzle 20 has a guide member K that unfolds inside out. Guide member K either aligns with or slightly hangs over the front passage opening 2011 of nozzle 20. There are a number of means to let guide member K unfold outwardly. For example, extend the front of air rod 9 slightly inward into the extension member 801 of insemination sheath situated in nozzle passage 201 and adhere the air hole 93 to the inner periphery of extension member 801; next carry out air extraction to let air hole 93 suck up the corresponding extension member 801; withdraw air rod 9 and the sucked extension member 801 is also pulled out to form a section of superimposed guide member K that unfolds inside out.

The nozzle 20 and catheter tube 10 of the invention are conventional assemblies. The insemination sheath 80 is inserted into nozzle passage 2011 after nozzle 20 and catheter tube 10 are assembled, so there is no friction between insemination sheath 80 and catheter tube 10.

Figure 15:
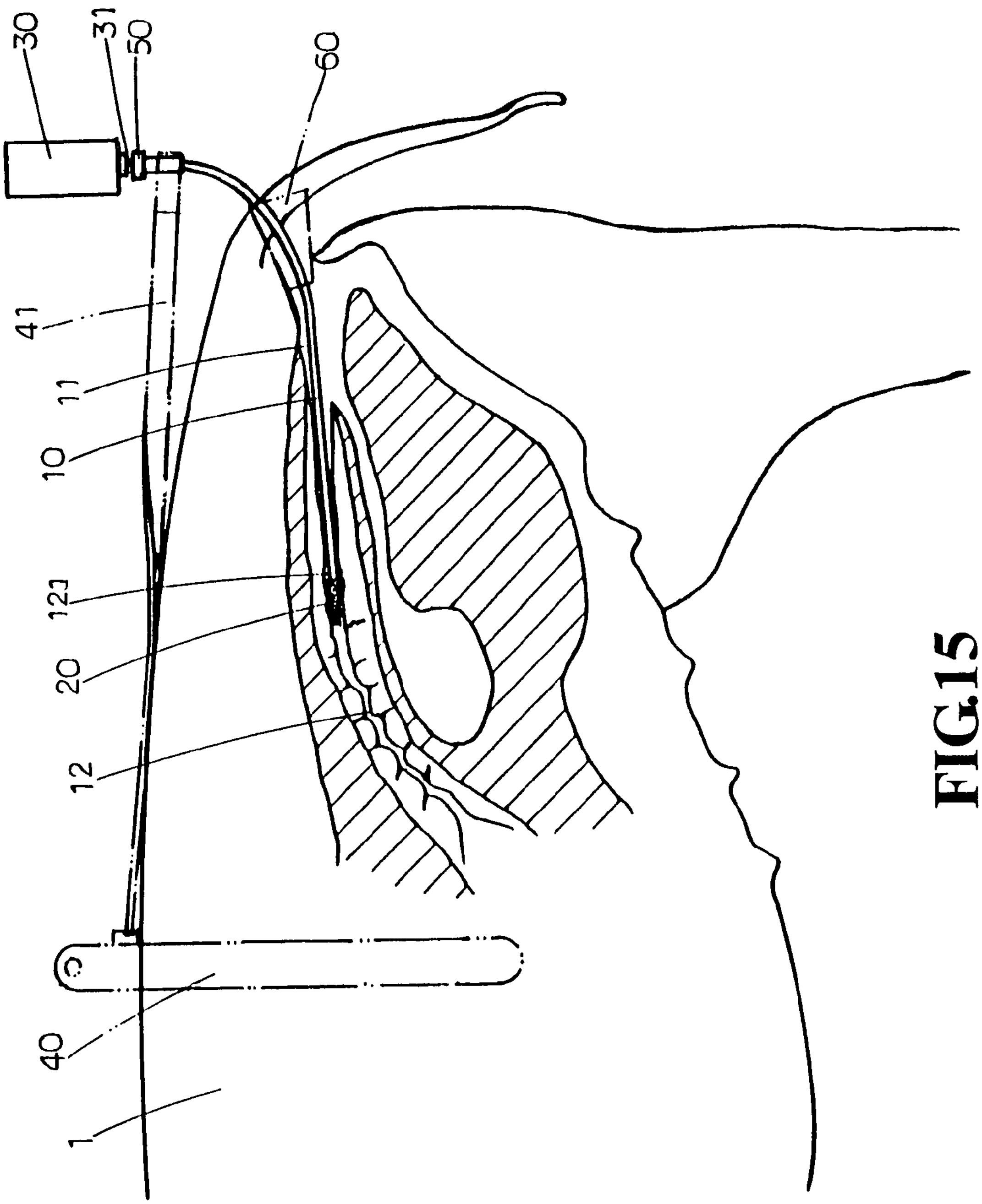
FIG. 15 shows the deployment of the invention in the body of a female animal.

Referring to FIG. 15, the operator would use conventional operating procedure when using the present invention for artificial insemination in animals. That is, the nozzle 20 and catheter tube 10 are inserted into the vagina 11 of animal body 1 through guide bush 60, where nozzle 20 is extended approximately to the position of first cervical ring 121 of cervical tract 12, and connector 50 at the rear end of catheter tube 10 is bent upward as in prior art to secure to the positioning strap 41 of AI Buddy 40, and the insertion tube 31 of semen dispenser (bag or syringe) 30 is inserted into connector 50 and pulled out after proper amount of semen fluid is squeezed into catheter tube 10.

Figure 14:
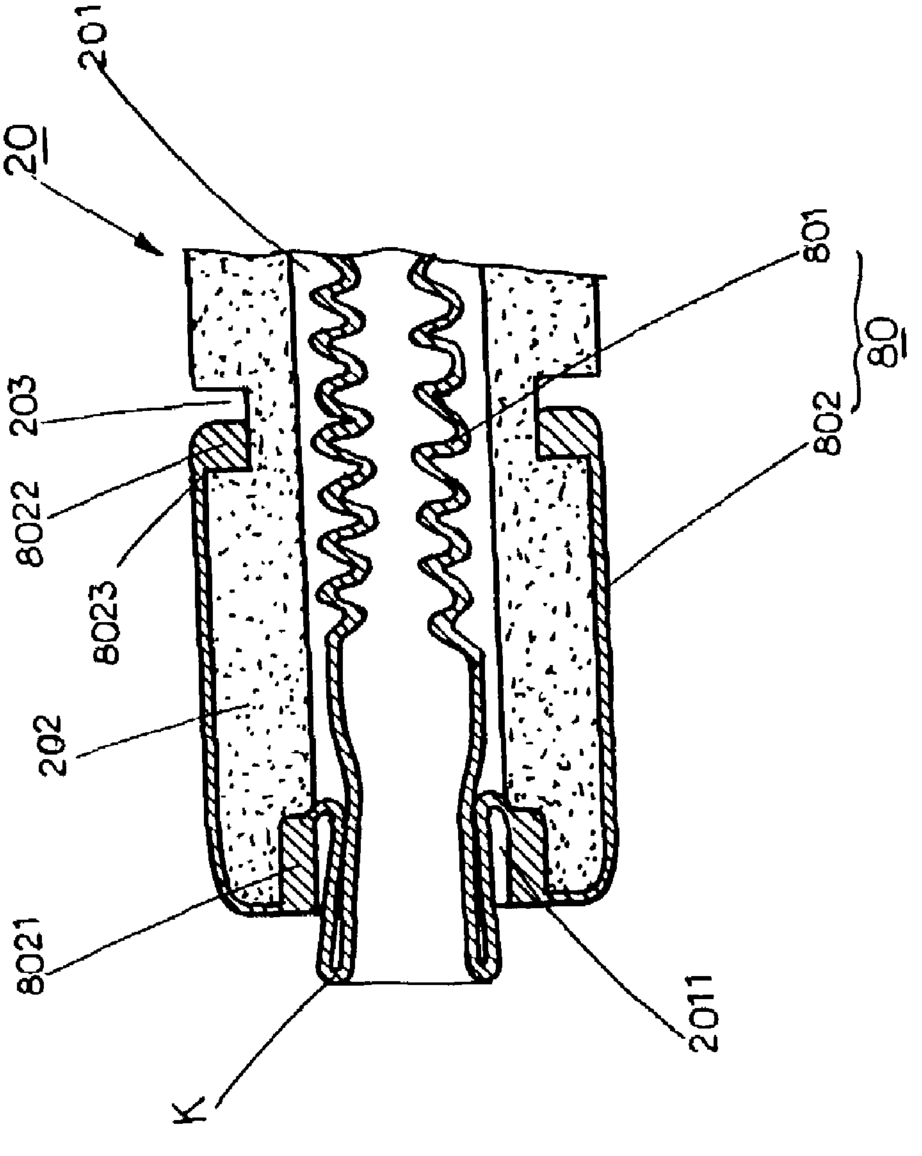
FIG. 14 is a schematic view of the elastic insemination sheath according to the invention conjoining the nozzle and forming a guide member that unfolds outwardly.
Figure 16:
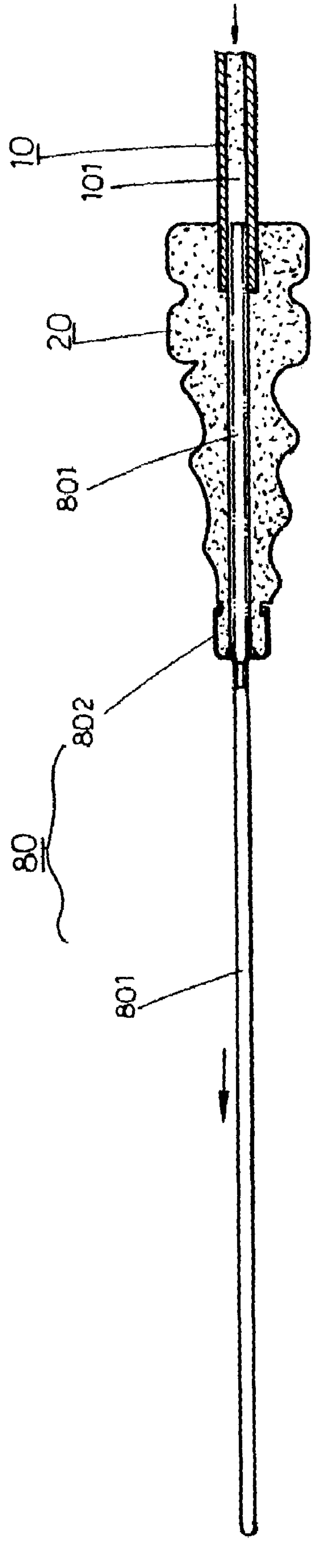
FIG. 16 is a schematic view of the elastic insemination sheath according to the invention extending outwardly.
Figure 17:
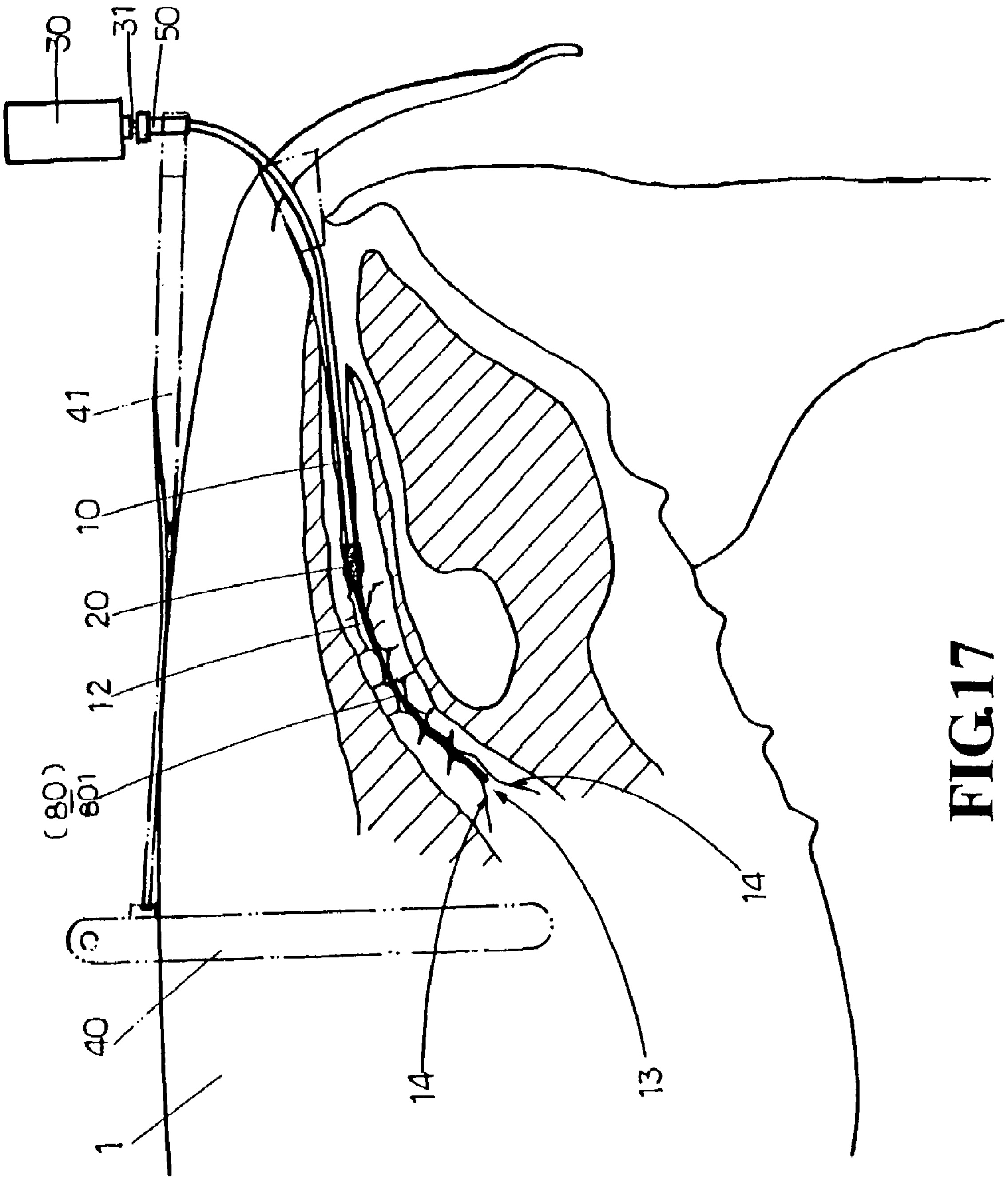
FIG. 17 shows the deployment of the invention in the body of a female animal with insemination sheath unfolded.

Referring to FIG. 16 and FIG. 17, when the semen in semen dispenser (bag or syringe) 30 is squeezed into catheter tube 10, the extension member 80 compressed between nozzle passage 201 and forward portion of center orifice 101 of catheter tube is pushed forward automatically under pressure. Under the guidance of guide member K which is a section of extension member 801 situated at the nozzle passage opening 2011 and unfolds inside out (FIG. 14), extension member 801, under the force of semen, will extend forward and outward (FIG. 16) to allow semen from catheter tube 10 to enter. As shown in FIG. 17, when the semen dispenser (bag or syringe) squeezes semen into catheter tube 10, the extension member 801 of insemination sheath 80 will be filled with semen and extend from the front part of nozzle 20 forward and outward towards cervical tract 12 and directly engages the two ducts to uterine horns 14 or the uterus 13. Because the extension member 801 of insemination sheath is soft and pliable, it could extend forward under pressure along the circuitous and narrow cervical tract without causing friction. Such design allows the front part of extension member to reach deep into cervical tract 12 to the two ducts to uterine horns 14 or uterus 13 without traumatizing the delicate tissue of cervical tract 12 or hurting the animal, rendering the artificial insemination process safer and more humane.

Figure 18:
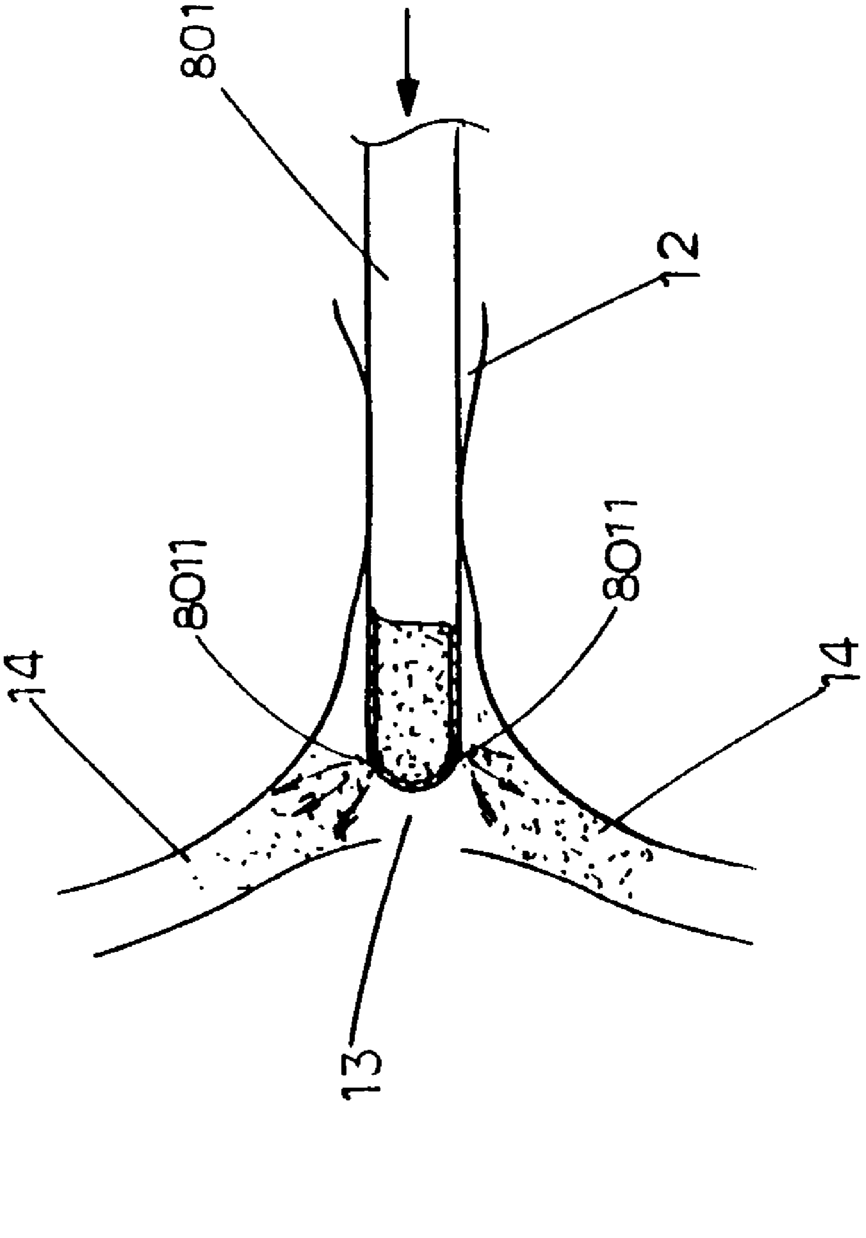
FIG. 18 shows the front part of insemination sheath extending into the uterus of a female animal according to the invention

When extension member 801 extends and its front part enters uterus 13 or the two ducts to uterine horns 14, it will be squeezed under uterine contraction and the semen inside is also pushed forward. The front part of extension member 801 has two juxtaposing slits 8011, which are forced open when semen is pushed forward (as shown in FIG. 13 and FIG. 18) so that semen is rapidly expelled into the two ducts of uterine horns 14 or uterus 13. Subsequently as the uterus continues to contract, semen inside the extension member 801 is gradually emptied, and semen injected into catheter tube 10 also continues to enter the extension member 801 of insemination sheath to enhance the efficiency of artificial insemination.

Given that the two slits 8011 on the front part of extension member 801 are in closed state while not under squeeze force, they are kept closed during the stage of semen being injected into catheter tube 10 and extension member 801 of insemination sheath gradually unfolding. When extension member 801 extends through cervical tract 12 and reaches the two ducts to uterine horns 14 or uterus 13, the slits will open under pressure and release the semen. As such, semen is used most efficiently.

The insemination sheath 80 may be coated a layer of lubricant inside and outside during fabrication, which will facilitate the insertion and withdrawal of air rod 9, and makes its enfolding over the positioning member 202 of nozzle a simple and convenient procedure. The lubrication helps in particular the forward extension of extension member 801 into cervical tract 12 to keep the process smooth and swift.

Because the strap member 802 of insemination sheath 80 is securely seated in the seat groove 203 on the positioning member 202 of nozzle 20 through strap ring 8022 and strap edge 8023, the insemination sheath will not dislodge when extension member 801 extends forward to cervical tract 12 and uterus 13 of female animal body 1 under squeeze force.

Figure 1:
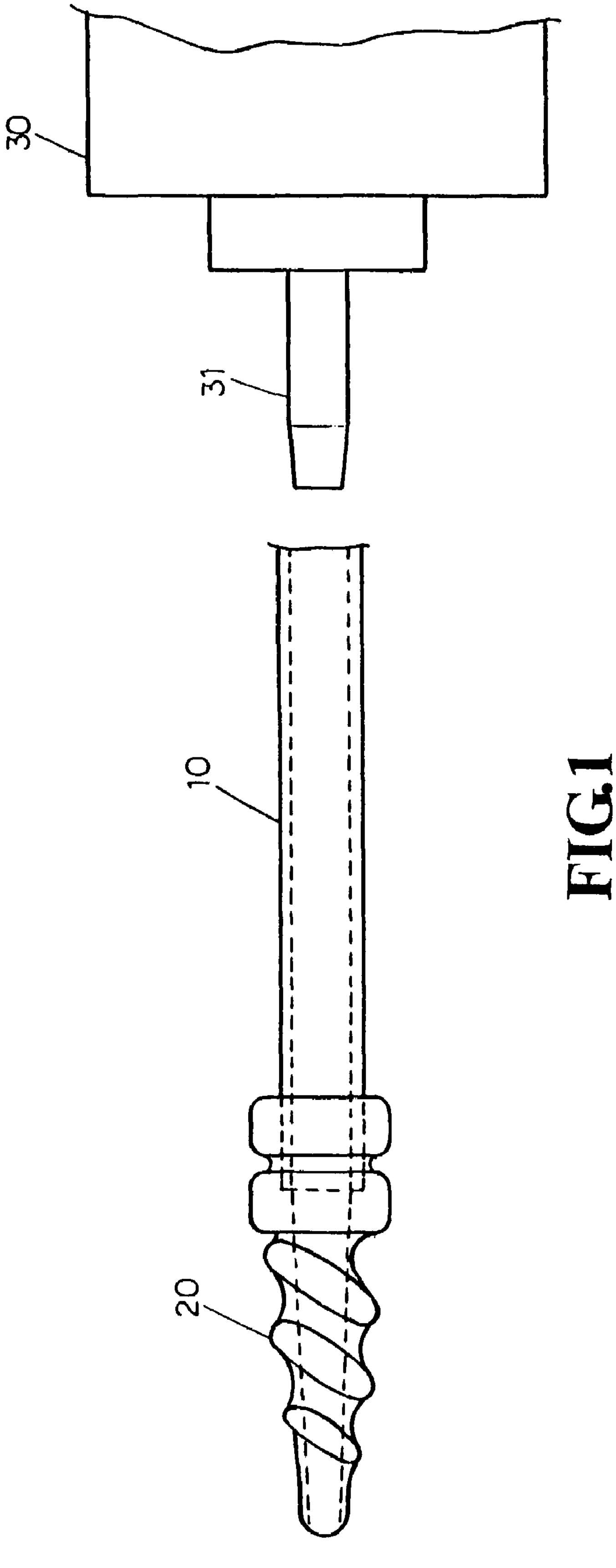
FIG.1 PRIOR ART
FIG. 1 is a schematic of a conventional artificial insemination device with a semen dispenser.
Figure 2:
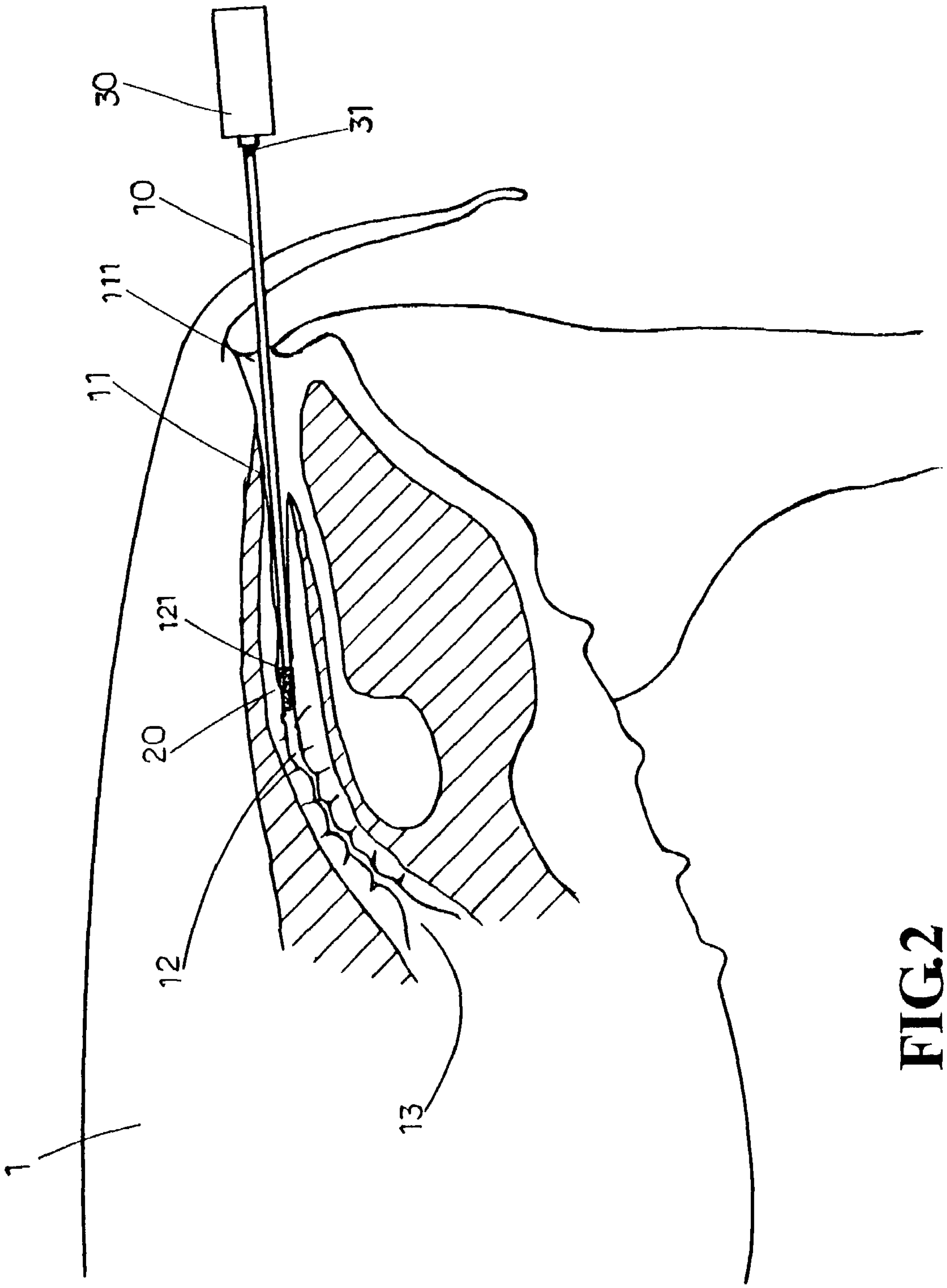
FIG.2 PRIOR ART
FIG. 2 is a schematic of the artificial insemination device in FIG. 1 penetrating the body of a female animal.
Figure 3:
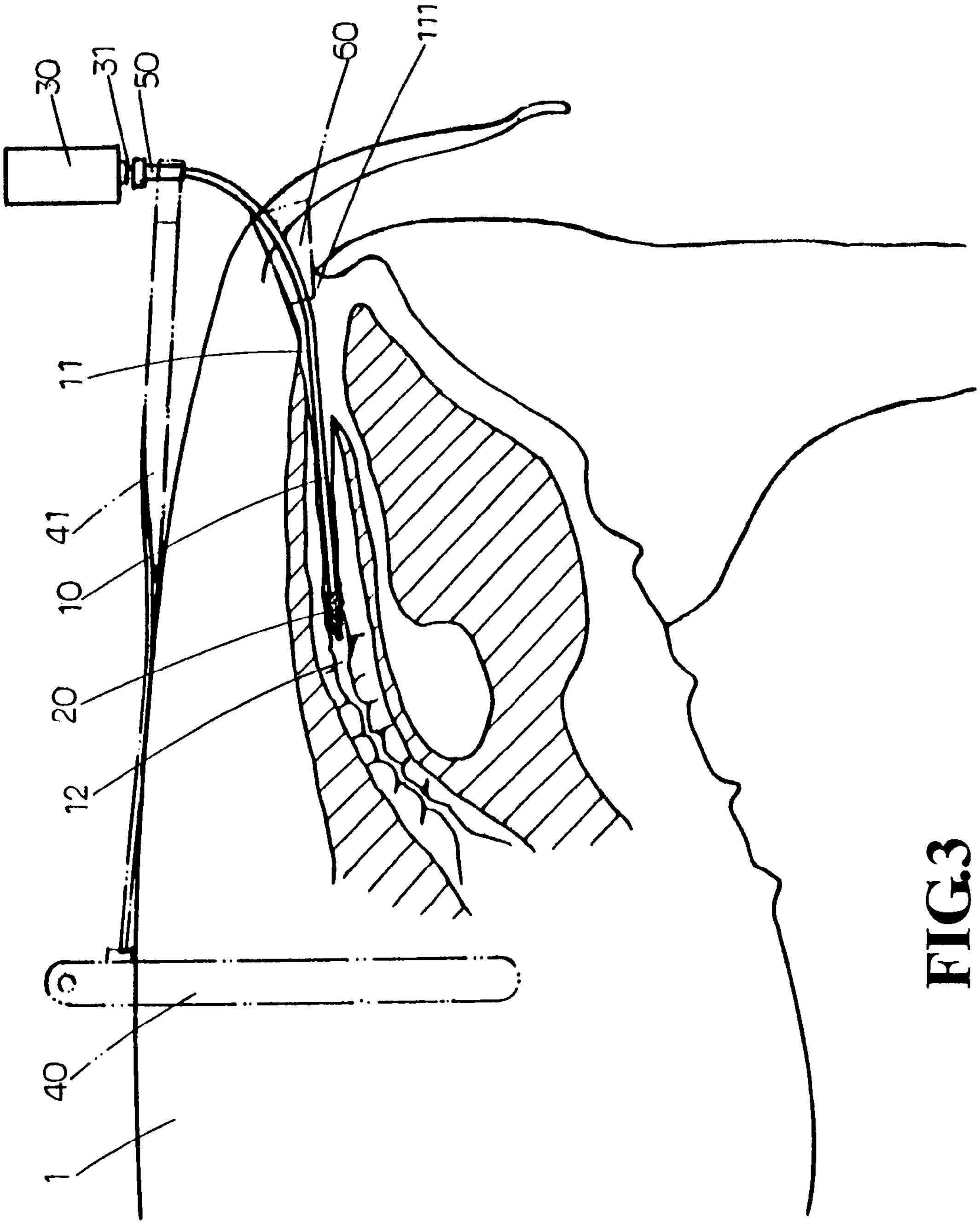
FIG.3 PRIOR ART
FIG. 3 is a schematic of a conventional artificial insemination device, equipped with a connector and an AI Buddy, penetrating the body of a female animal.
Figure 4:
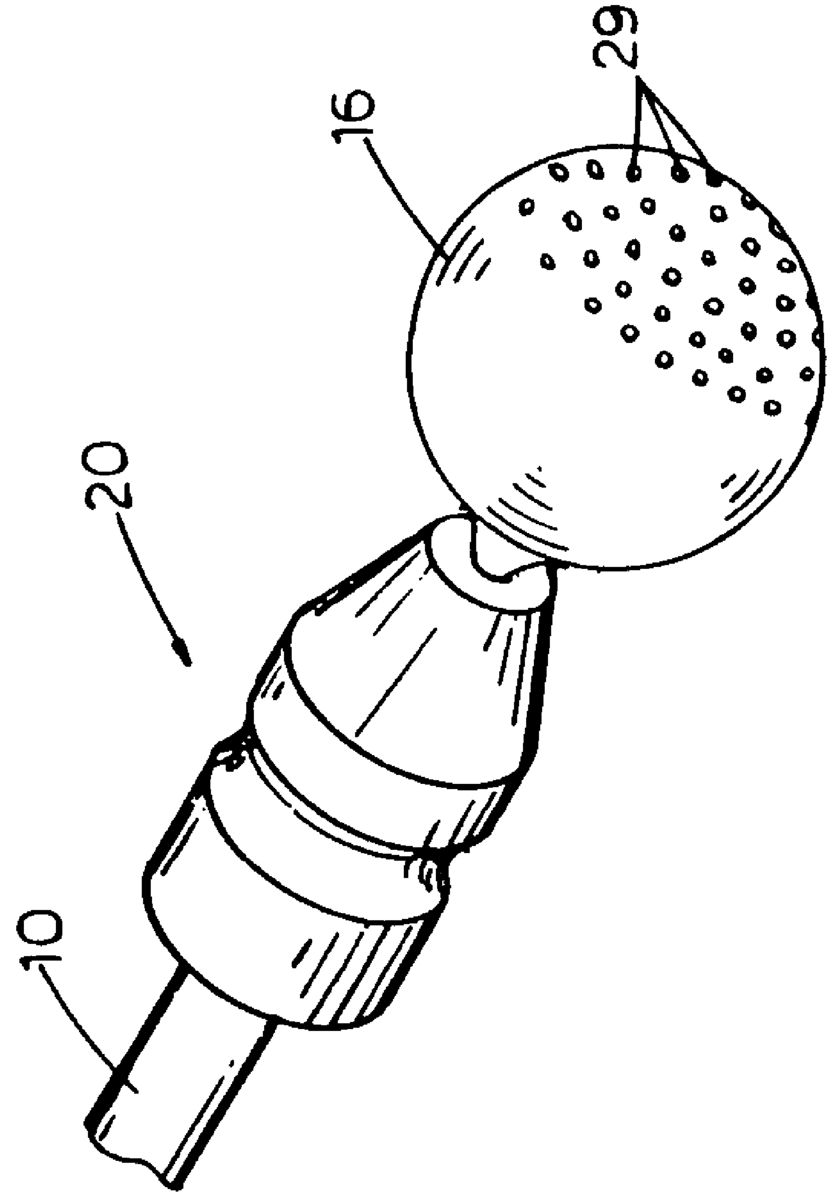
FIG.4 PRIOR ART
FIG. 4 is a perspective view of an artificial insemination device disclosed in U.S. Pat. No. 5,899,848.
Figure 5:
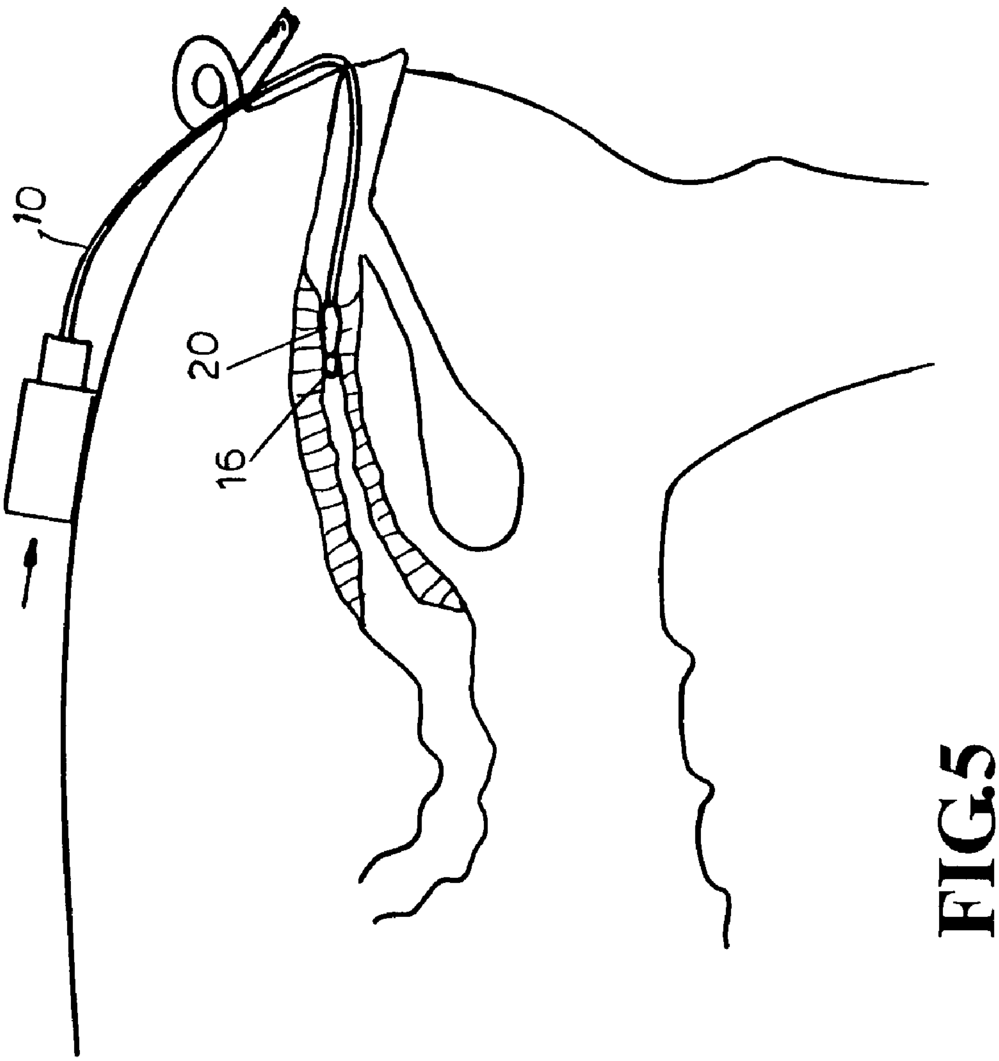
FIG.5 PRIOR ART
FIG. 5 is schematic of the artificial insemination device in FIG. 4 showing its placement inside the body of a female animal.
Figure 6A:
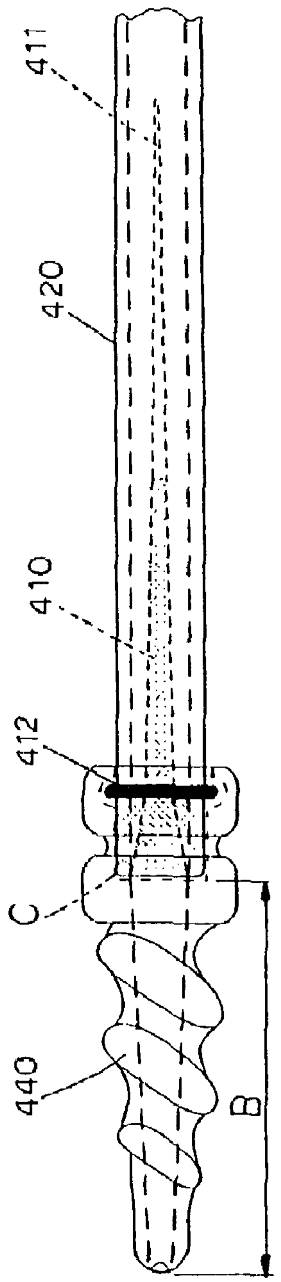
FIG.6A PRIOR ART
FIGS. 6A and 6B are schematic views of the before and after deployment, respectively, of the catheter in accordance with the artificial insemination device disclosed in U.S. Pat. No. 6,526,917.
Figure 6B:
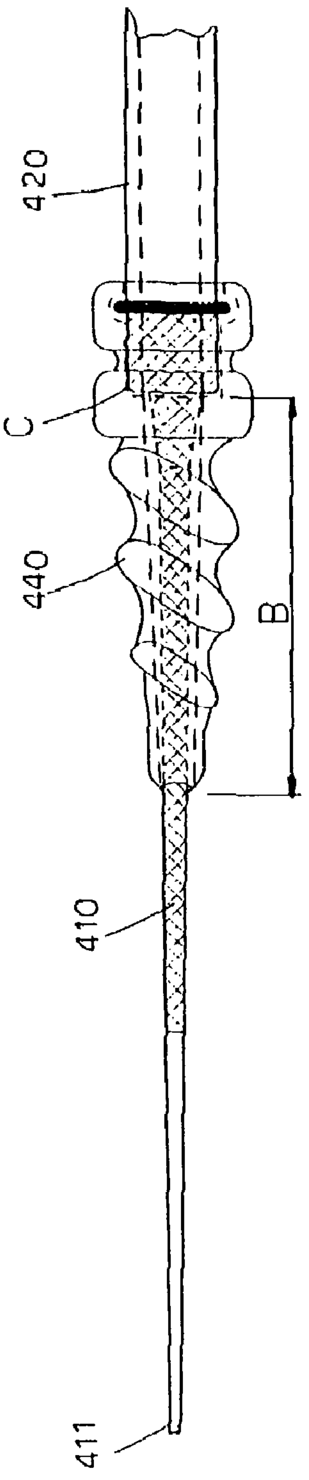
FIG.6B PRIOR ART
Figure 7A:
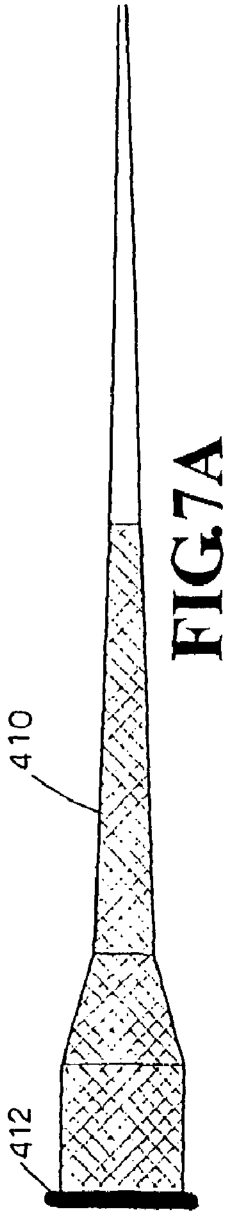
FIG.7A PRIOR ART
FIGS. 7A through 7F show the assembly of the catheter of FIGS. 6A and 6B.
Figure 7B:
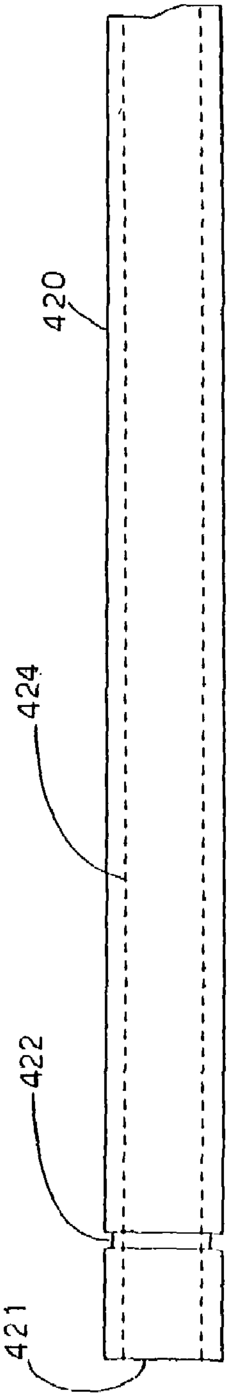
FIG.7B PRIOR ART
Figure 7C:
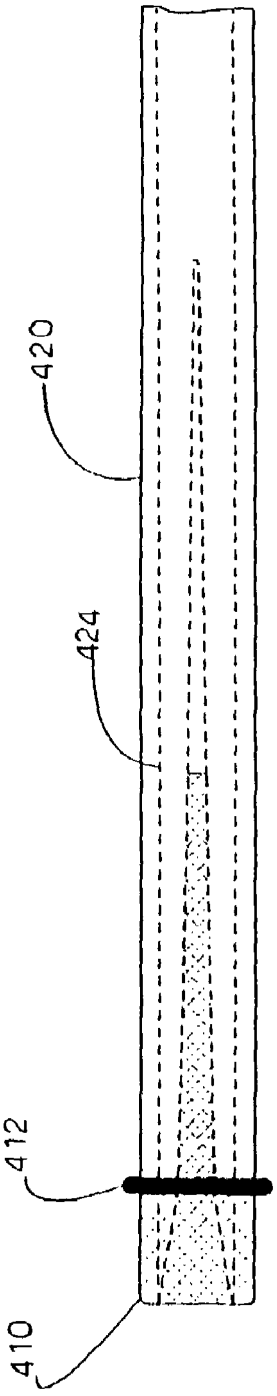
FIG.7C PRIOR ART
Figure 7D:
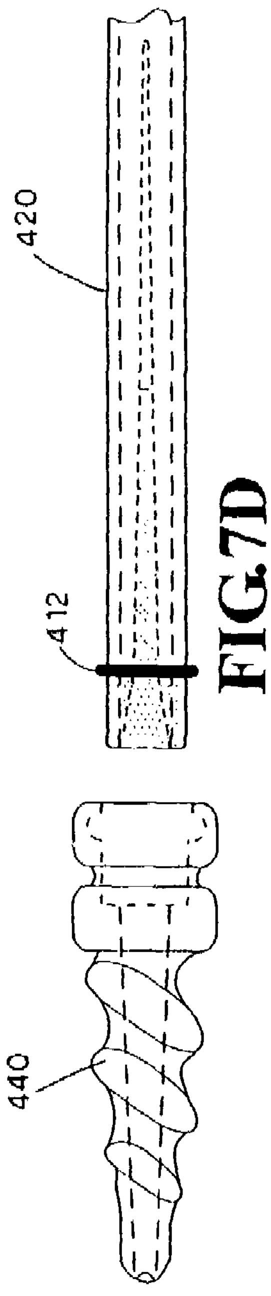
FIG.7D PRIOR ART
Figure 7E:
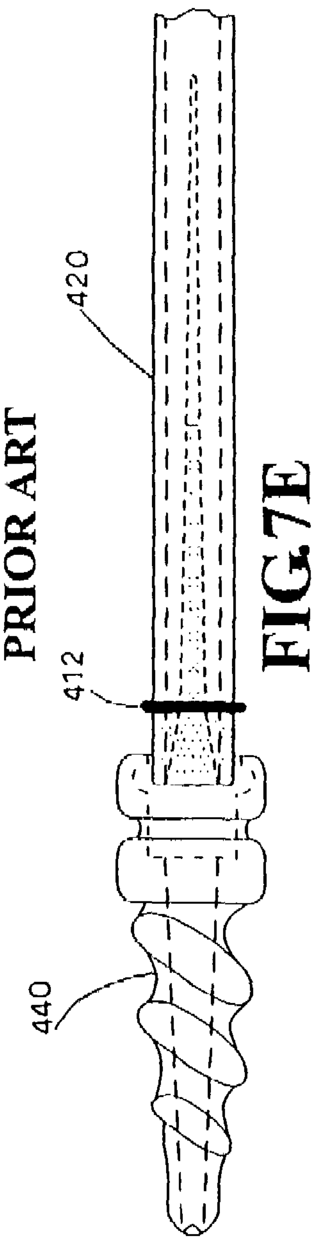
FIG.7E PRIOR ART
Figure 7F:
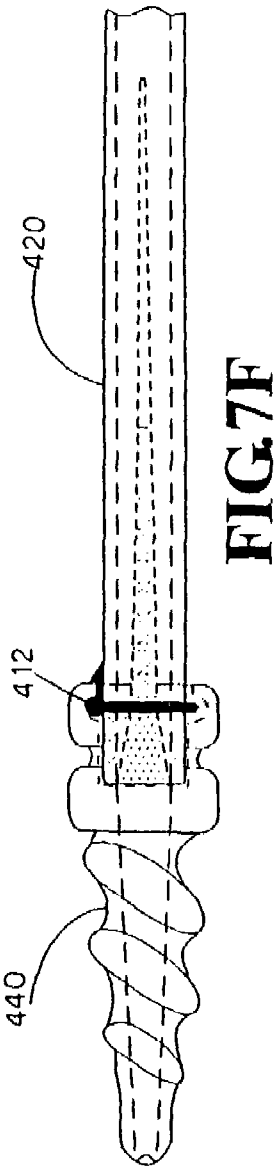
FIG.7F PRIOR ART

The extension member 801 of insemination sheath 80 is inserted into nozzle 20 through its front passage opening 2011 and the strap member 802 of insemination sheath 80 enfolds tightly over the front part of nozzle 20, instead of being secured at the junction of catheter tube and nozzle 20 as in prior art (FIG. 6 and FIG. 7). Such arrangement is less likely to cause perforation in insemination sheath and makes it easier to check the effect of insemination. More particularly, when nozzle 20 reaches the position of first cervical ring 121 of cervical tract, the distance to travel by extension member 801 into uterus 13 is measured from the front of nozzle 20, instead of the front of catheter tube as in prior art. As the distance to travel is apparently shorter, extension member 801 will be able to reach uterus 13 more swiftly and smoothly under pressure. In addition with an outward-unfolding guide member K at the passage opening 2011 of nozzle by extension member 801, only small pressure from the injection of semen into catheter tube 10 is needed to cause the extension member 801 to extend forward and outward quickly and smoothly, which is an improvement over prior art that requires greater exertion of force.

As described above, the extension member 801 of insemination sheath 80 is conveniently tucked into the nozzle 20 through its front passage opening 2011 and is compressed in shorter length between nozzle passage 201 and the forward portion of center orifice 101 of catheter tube 10. This is a contrast to prior art that requires longer sheath and the sheath needs to be placed entirely inside the catheter tube. As such, the extension member 801 of insemination sheath 80 according to the present invention can have smaller diameter, and the center orifice 101 of the catheter tube can also be made smaller. As such, the extension member 801 can quickly deliver semen into uterus 13 under minimal squeeze force and the aid of uterine contraction. Consequently, there is no need to massively dilute the semen or use catheter tube of larger diameter in order to accommodate large volume of diluted semen fluid as in prior art. Instead, only small amount of more concentrated semen is required to fill the tube of smaller diameter. Thus the present invention offers the economic benefit of saving semen, and concurrently, raises the fertilization rate and number of fetus, thereby allowing successful insemination with minute amount of semen.

Because the strap member 802 of insemination sheath 80 has a more rigid neck ring 8021 disposed at the front passage opening 2011 of nozzle 20 as support, the front part of nozzle 20 is kept soft at the outer periphery, while the passage opening 2011 at the center is not prone to deformation. Consequently in the process of artificial insemination, the nozzle passage opening 2011 will not bend, deform or even block the outward extension of extension member 801 due to improper exertion of force or the fidgeting of animal to ensure a smooth process.

In other words, the invention disclosed herein has at least the following advantages:

1. The extension member of insemination sheath is tucked into nozzle directly through its front passage opening and amassed in compressed state between the forward portion of center orifice of catheter tube and nozzle passage, and the strap member at rear section of elastic insemination sheath is secured to the front part of nozzle. Thus when semen is squeezed into the catheter tube which causes the insemination sheath to unfold gradually under pressure, the length of insemination sheath that enters into the uterus along cervical tract is actually shorter as measured from the front part of nozzle. As such, the pressure needed to push the insemination sheath outward is effectively reduced, which renders the practice of artificial insemination more convenient. Similarly, the movement of insemination sheath extending into the uterus is also made smoother, thereby enhancing the efficiency of artificial insemination.

2. The strap member of insemination sheath is secured directly to the front part of nozzle, instead of at the junction of nozzle and catheter tube. Such arrangement makes it easier to check the effect of insemination and less likely to cause perforation.

3. Because the strap member of elastic insemination sheath has a more rigid neck ring disposed at the front passage opening of nozzle as support, the front part of nozzle is kept soft at the outer periphery, while the passage opening at the center can be free of deformation, bending or blocking the passage of catheter tube to increase the chance of successful insemination.

4. The extension member of elastic insemination sheath is tucked into the front part of nozzle and amassed in compressed state between the nozzle passage and the forward portion of center orifice of catheter tube, instead of being inserted completely into the catheter tube. As such, the inner diameter of the extension member and catheter tube can be made smaller. Also, as the extension member can deliver semen swiftly into uterus without the concern of backflow, the semen used does not require massive dilution, while only more concentrated semen in small amount needs to be injected into the catheter tube. Thus the present invention not only offers the economic benefit of saving the semen used, the fertilization rate and the number of fetus are also expected to increase.

5. After the extension member of insemination sheath is amassed in compressed state in nozzle passage, the portion of extension member situated at the passage opening has a guide member that unfolds in an inside-out manner. When semen is squeezed into the catheter tube and applies pressure on the extension member, the guide member concurrently guides the whole assembly of extension member to unfold inside out and extend forward in a swift and smooth manner.

What is claimed is:

1. An artificial insemination device for animals, comprising: a catheter tube, a nozzle, a connector, and an elastic insemination sheath;

the nozzle extending from the catheter tube, said nozzle having a terminal front positioning member end, the connector being installed posterior to the catheter tube for the insertion of an insertion tube of a semen dispenser;

the elastic insemination sheath having an extension member extending from a strap member; said strap member of said elastic insemination device being greater in radial extent than the extension member and having a thickened strap ring adjacent a tapered strap edge; said extension member having an elongated shape and being tucked inwardly through a front passage opening into a passage of the nozzle and amassed in a compressed state within the nozzle passage and a forward portion of a center orifice of the catheter tube; said strap member being secured over the outer tip of the terminal front positioning member end, a neck ring portion of the strap member adjoining the extension member for bracing the terminal front positioning member end;

whereby, when semen is squeezed into the catheter tube from the semen dispenser, the extension member of the elastic insemination sheath extends from the compressed state outward through the terminal front positioning member end for entry into the cervical tract of female animal body to reach the uterus or the two ducts to the uterine horns.

2. The artificial insemination device for animals as claimed in claim 1, wherein a plurality of juxtaposing slits are formed at a front part of the extension member of said elastic insemination sheath.

3. The artificial insemination device for animals as claimed in claim 2, wherein a plurality of juxtaposing slits of the extension member are biased to a closed state and open responsive to pressure from uterine contraction.

4. The artificial insemination device for animals as claimed in claim 1, wherein the extension member of said elastic insemination sheath is less in outer diameter than the nozzle passage and the center orifice of the catheter tube.

5. The artificial insemination device for animals as claimed in claim 1, wherein after the extension member of said elastic insemination sheath is amassed in a compressed state between the nozzle passage and the forward portion of the center orifice of the catheter tube, a superimposed guide member folded in an inside-out manner is disposed at the front passage opening of the nozzle.

6. The artificial insemination device for animals as claimed in claim 5, wherein said guide member is disposed to protrude beyond the front passage opening of the nozzle.

7. The artificial insemination device for animals as claimed in claim 1, wherein the strap member of said elastic insemination sheath enfolds over the front positioning member end, the thickened strap ring and strap edge retentively engaging a prearranged seat groove formed in the terminal front positioning member end.

8. The artificial insemination device for animals as claimed in claim 1, wherein the extension member is collapsibly gathered in when amassed in said compressed state.

* * * * *